United States Patent [19]

Froehlich et al.

[11] 4,166,094
[45] Aug. 28, 1979

[54] AUTOMATIC FLUID SAMPLING TRANSPORT SYSTEM

[75] Inventors: John A. Froehlich, West Redding; Roman Czernik, Bridgeport; Chester G. Fisher, III, Southport, all of Conn.

[73] Assignee: The Perkin-Elmer Corporation, Norwalk, Conn.

[21] Appl. No.: 907,450

[22] Filed: May 22, 1978

[51] Int. Cl.² .............................................. G01N 1/14
[52] U.S. Cl. .................................... 422/64; 73/425.6; 141/130; 422/100
[58] Field of Search ................. 23/230 R, 253 R, 259; 73/425.6; 141/130

[56] References Cited

U.S. PATENT DOCUMENTS

| | | | |
|---|---|---|---|
| 3,252,330 | 5/1966 | Kling | 23/253 R |
| 3,567,393 | 3/1971 | Welch | 23/253 R |
| 3,570,555 | 3/1971 | Gilson | 23/253 R |
| 3,609,040 | 9/1971 | Kuzel et al. | 23/253 R |
| 3,767,364 | 10/1973 | Ritchie et al. | 23/253 R |
| 3,801,283 | 4/1974 | Shapiro et al. | 23/253 R |
| 3,814,582 | 6/1974 | Rohrbaugh et al. | 23/253 R |
| 3,900,289 | 8/1975 | Liston | 23/253 R |
| 3,969,079 | 7/1976 | Catarious et al. | 23/253 R |

*Primary Examiner*—R. E. Serwin
*Attorney, Agent, or Firm*—Salvatore A. Giarratana; Francis L. Masselle; Thomas P. Murphy

[57] ABSTRACT

An automatic fluid sampling transport system for use in fields such as atomic absorption spectroscopy and liquid chromatography. The system described provides for circular tray sampling having an increased through-put capacity. This is accomplished by providing a system which allows the sampling of vials in concentric circles on the same carousel. The mechanism described synchronizes the raising and lowering of the sample probe to the incremental, rotational movement of the carousel and the rotational movement of the probe carrying means between successive sample vials in the various concentric circles. The mechanism is relatively simple and is adaptable to provide a plurality of such concentric circles of openings to expand the through-put capability of the system.

10 Claims, 4 Drawing Figures

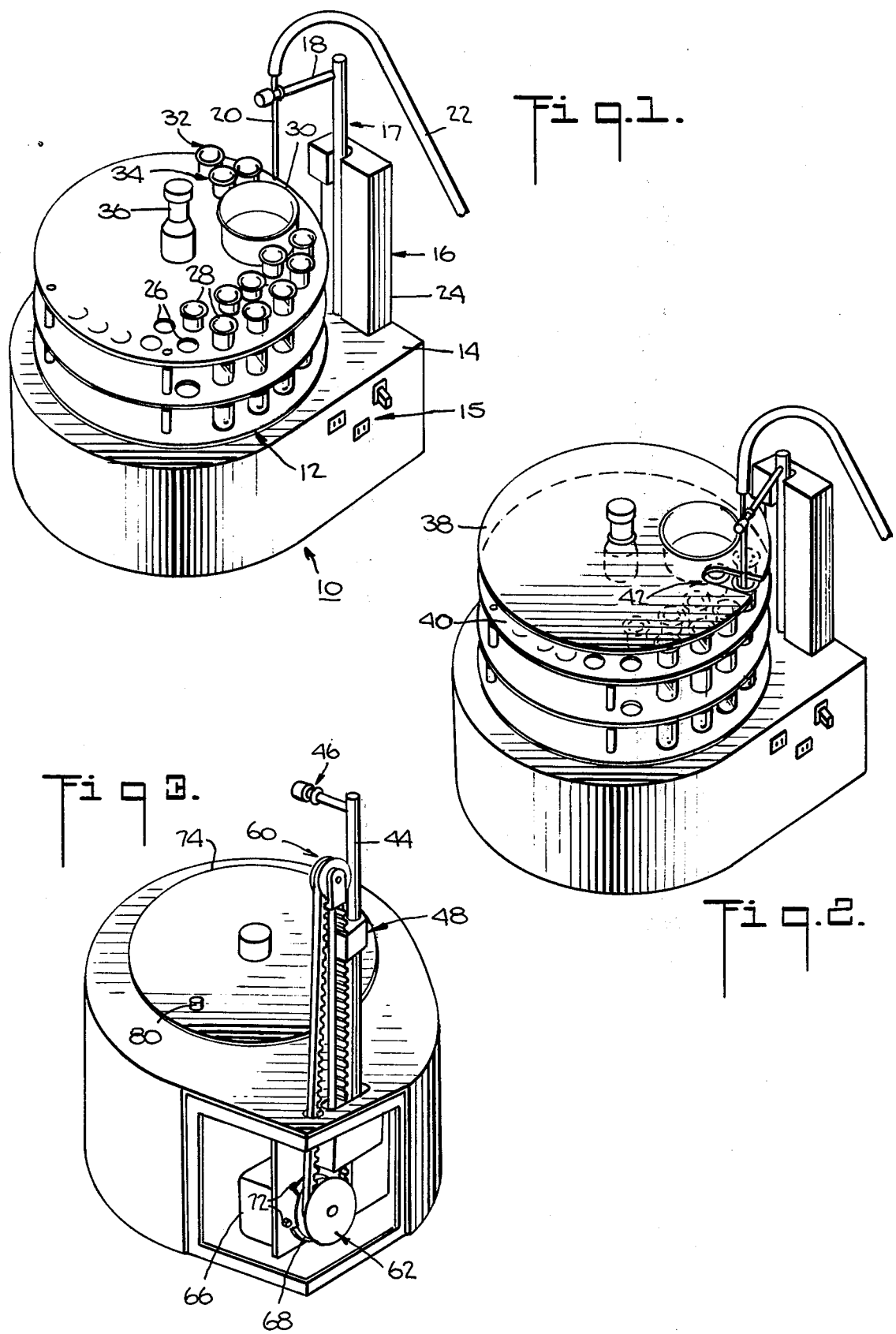

AUTOMATIC FLUID SAMPLING TRANSPORT SYSTEM

FIELD OF THE INVENTION

This invention pertains generally to the fluid sampling field, and more particularly, to a circular tray sampler which is most suitably adapted for use in the atomic absorption spectroscopy and liquid chromatography fields.

BACKGROUND OF THE INVENTION

Fluid sampling extends over a wide range of fields, including atomic absorption spectroscopy and liquid chromatography. In these latter fields, unknown elements in solution are supplied in sample test tubes which are sequentially analyzed by the parent instrument.

Ideally, many vials of sample are pre-arranged in trays or racks for positioning on a sampler platform which cooperates with the instrument in sequentially analyzing the solution in each vial. Typically, the sample vials are disposed in a circular tray or in linear racks.

Heretofore, the circular tray arrangements provided for a singular circular row disposed near the perimeter of the tray. Typically samplers introduce the sampling probe into the vials in either an arcuate type motion or with an up-down motion interspersed with a step positioning of the tray so as to sample successive vials. A typical example of a circular tray sampler with a single row of test vials and an up-down motion is described in U.S. Pat. No. 3,546,946.

Generally, the access time for the probe to leave one vial and thereafter access a second vial should not be a limiting factor in the operation of the overall system. In other words, it should be the actual analyzing instrument itself which controls the time for analysis and not the time required to access each successive vial. For example, in the field of atomic absorption spectroscopy, the analysis time for typically sized samples would be approximately 5 seconds. Therefore, the time between sample access should be less than this so that upon completion of a first analysis, the sampling equipment is ready to provide the subsequent specimen.

Further, the so-called through-put of the system (the number of sample vials processed per unit of time) can be enhanced and the total analysis time reduced if the vial density for each tray is increased. Further, with respect to the vials employed, the cost of a system can be reduced if the sampler employs standard test tubes, for example, the 15 milliliter size readily available from equipment supplies.

Of course, in increasing the vial handling capacity of the tray, the size should not be so large as to make its handling cumbersome. Also, it is desirable that the tray with the vials in place be removed as a unit from the sampler platform and a substituted tray disposed thereon to again speed up the analysis of the total number of sample vials.

Of course, the simpler the mechanics to implement such a system, the more reliable the overall system.

It is therefore a primary object of this invention to provide a fluid sampler which improves the vial through-put capability of a sample analysis system.

It is still another object of this invention to provide a relatively simple mechanical device for improving the fluid sampling through-put.

It is yet another object of this invention to provide a fluid sampler employing a circular tray, wherein the vial density per tray is increased without significantly increasing the overall dimensions of the circular tray.

SUMMARY OF THE INVENTION

Towards the accomplishment of the above and other objects which will become apparent from the following discussion, there is described herein an automatic fluid sampling transport system employing sample vials to be analyzed by appropriate analysis equipment. The invention comprises sample holding means which includes a plurality of openings disposed in at least two concentric circles of said openings into which are disposed corresponding sample vials. Means are disclosed for rotating the sample holding means. Probe carrying means are provided which accommodate particular type probes used in atomic absorption spectroscopy and liquid chromatograph. Means are described for raising and lowering the sample probe carrying means and for rotating said probe carrying means a predetermined arcuate length from a cooperating position with a sample vial in an opening on one concentric circle to a cooperating position with a sample vial in an opening in another concentric circle. The means for raising and lowering the sample probe are synchronously operated with the means for rotating the probe carrying means so that the respective operations are performed sequentially. Further, the raising and lowering and rotating are meshed with the rotation of the sample holding means so that the entire operation is automatic. The synchronous movement is effected by a cooperative operation between a belt driven assembly for raising and lowering the probe carrying means; geneva wheel assembly for incrementally positioning the carousel; and a cam-arm arrangement for converting the rotational movement imparted to the sample holding means to rotational movement of the same probe carrying means so as to result in the positioning of the latter in cooperative relationship with sample vials in alternating concentric circles.

BRIEF DESCRIPTION OF THE DRAWINGS

FIG. 1 is a perspective view of the assembly of this invention.

FIG. 2 is essentially the same perspective view as FIG. 1 showing a cover in place over that assembly.

FIG. 3 is a perspective view of a portion of the assembly of the invention with the carousel and part of the external covering removed.

DESCRIPTION OF THE PREFERRED EMBODIMENT

Figure 4:
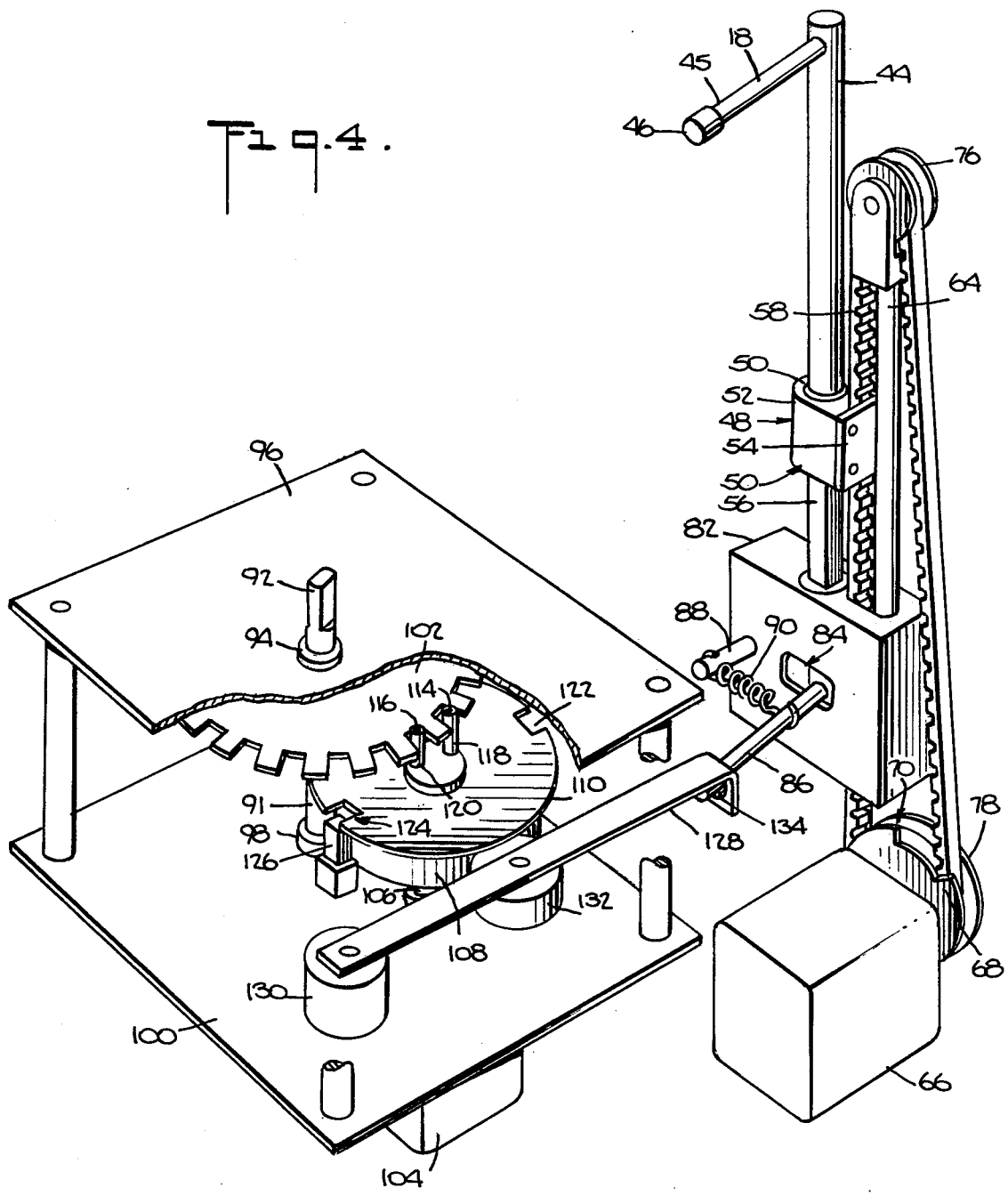
FIG. 4 is a perspective view, in section, of the internal mechanics of the assembly and illustrating the cooperative action of the elements of the invention.

Referring now to FIG. 1 there is shown a perspective view of the autosampler assembly of the present invention. The sampler, 10, includes a sample holding means (hereinafter "carousel" or "circular tray") which is disposed upon a platform or turntable on console 14. The console 14 includes appropriate electrical interface connections and powering switches 15. The interface connections supply the necessary electrical information from the system control panel, which allow the automatic processing of the samples and other additional features.

The console has appended thereto a probe positioning assembly 16. This comprises probe carrying means 17 including horizontal probe arm 18 which retains a probe 20. Connected thereto is a piece of flexible, capillary tubing 22. The latter connects the sample probe to the analyzing instrumentation, e.g., a nebulizer for an atomic absorption spectrophotometer. The mechanics for raising and lowering the probe carrying means is housed partially within cover 24, and will be described more particularly in the discussion of FIGS. 3 and 4.

The carousel 12 as shown in a three-tier arrangement and is seen to include a plurality of suitably sized circular openings 26 into which are disposed sample test tubes 28. The holes are sized to accommodate standard vials such as a 15 milliliter test tube, which are readily available from equipment suppliers.

For the embodiment described, the holes are disposed in two concentric circles, with the openings for the inner circle disposed opposite the spaces between openings on the outer circle. This arrangement accommodates the arcuate swing of the probe carrying means between the outer and inner circle. The concentric circles are labeled 32 and 34 in FIG. 1.

The fact that there are only 2 such concentric circles shown in the figure is not to be construed as a limitation of the present invention. More concentric circles than just two are within the scope of this invention and would be an obvious extension of the present design and the mechanics needed to implement the design and as discussed hereinafter with respect to FIG. 4.

Further, the carousel 12 is seen to include a handle 36 which facilitates the removal of the tray from the turntable.

Also, it is seen to include a larger opening into which is positioned a beaker 30, containing, e.g., a sample-free wash solution. This would be employed at start-up to stabilize the equipment. E.g., the flame condition of the burner for the atomic absorption spectrophotometer, which is connected to the sampler through a nebulizer and copallary tubing 22, is stabilized by first running the sample-free solution through. This is a desirable step prior to calibrating the equipment and, thereafter, analyzing the samples.

Referring now to FIG. 2, essentially the assembly of FIG. 1 is depicted but with the sampling probe in a down position and disposed in one of the sample vials in the outside circle. Further, the figure shows the placement of a tray cover over the top of the tray. The cover is supported so as to allow the tray to rotate underneath without rotating. The cover 38 retards evaporation of the sample and avoids contamination thereof. Opening 42 is provided at the point of the probe to allow access to the particular sample in either circle.

FIG. 3 shows in perspective view, the sampler with the carousel 12 removed as well as the cover 24 and a portion of the console 14. FIG. 4 is a perspective view of the mechanics of the autosampler. The following discussion will involve both FIGS. 3 and 4 interchangeably.

The probe carrying means 17 is seen to include a sleeve or tube 44 to which is secured arm 18. The probe is positioned in a hole 45 in the arm 18. It is retained by adjusting a nut-washer assembly 46 against it.

Tube 44 is secured to a belt retaining block assembly 48 by grip rings 50 on top and on the bottom of the block assembly 48. The block assembly includes a main portion 52 and plate portion 54 which is secured to the main portion by screws.

The tube block assembly rides up and down on a piece of square stock 56. This provides a linear bearing surface for the tube block assembly. The square stock typically is fabricated from aluminum and is coated with a relatively slippery but hard coating such as NI-TUFF a trademarked product of the Poly-Metal Finishing, Inc. of Springfield, Mass. The block assembly, and in particular the main portion 52 typically will be fabricated from bronze when the square stock is coated aluminum.

Alternately, the square stock 56 can be fabricated from stainless steel. In that case the block 52 has been fabricated from oxide coated, cold rolled steel. However, the latter combination has been found to have less durability than the previously described one.

Means for raising and lowering the probe sampling means are shown in FIG. 3 and more clearly in FIG. 4. It includes a toothed belt 58 which is driven between pulley assemblies 60 and 62. Assembly 62 is secured to the top of support rod 64 which is fastened to the console at its lower end. The lower pulley assembly 62 is driven by one of two AC reversible motors within the assembly. The motor is designated as 66 in FIGS. 3 and 4.

Pulley assembly 62 includes a disc member 68. For the embodiment shown, it has an approximate 45 degree segment 70 removed from its perimeter. The radial edges of this segment each cooperate with sensor means 72 (such as LED, optical switches) to sense the angular position of the pulley assembly, and consequently, the fact that the sample probe carrying means is either fully up or down. The switches cooperate with the power to the motor 66 and the programming electronics (external to the sampler) to first raise the probe carrying means and, after a suitable delay to swing the probe carrying means between the concentric circles to thereafter lower same into the next sample vial.

The toothed belt passes around pulleys 76 and 78 in assemblies 60 and 62 respectively. The belt is secured to the probe raising and lowering means by capturing it to the main block portion 52 of block assembly 48, by sandwiching it with plate 54.

Turntable 74 is seen to include a protrusion 80 for keying the carousel to the table and in turn to the program which directs the autosampler's operation.

Alternate approaches to the raising and lowering of the sample probe carrying means include use of a wire cable in place of the toothed belt with appropriate means for securing it to block assembly 48. Further, the raising and lowering of the probe carrying means can be affected by a motor-lead screw arrangement. This is somewhat impractical because of the necessity to have the lead screw driven at extremely high speeds to effect the raising and lowering times necessitated by the overall system design.

The FIG. 4 view reveals that enclosure 82 includes a slotted portion through which passes horizontal arm 86. The latter is press fitted or otherwise secured to the square stock piece 56 so as to rotate therewith as described hereinafter. (Square stock 56 is rotatably mounted in a bearing mounted on the underside of enclosure 82, and is not readily visible in any of the views).

Pin 88 is likewise press fitted into the slotted side of enclosure 82 and extends outward therefrom. It is grooved to accept the end loop of spring 90 and to retain it during the flexing of said spring. The other end of spring 90 is secured to the arm 86 by a grip ring, or groove, or the like.

FIG. 4, with the console removed and portions of the internal mechanism partially sectioned, exposes the geneva wheel assembly of the invention. This assembly effects rotation of the sample holding means through the shaft 91. Further, FIG. 4 reveals the relatively simple mechanics utilized to rotate the sample probe carrying means a prescribed arcuate length between successive vials in the inner and outer circle of samples.

The sample holding platform or turntable, 74 in FIG. 3, mounts on end 92 of the table shaft 91. The latter is pivoted by a suitable bearing 94 in the top plate 96 of the geneva assembly and by bearing 98 in the bottom plate 100. Geneva wheel 102 is secured to the shaft 91 by means of a pressed-in hub and pin, not shown.

Drive power for the geneva assembly is provided by the second of the AC motors in the assembly, 104, through motor drive shaft 106. Connected to the upper end of the shaft 106 is an actuator cam 108. Secured upon the latter is a disc 110 and fastened to the top side of the disc is a mount 112 including pins 114 and 116 extending upwards therefrom. Positioned on these pins are detent rollers 118 and 120 which are held in place by suitable clips (not shown for clarity purposes), which allow the rollers to turn on the pins.

Disc 110 is provided with two cutouts, 122 and 124. These are 180° apart and located on the periphery of the disc. These cutouts cooperate with a sensing means, 126, which can be an optical sensing switch similar to sensors 72 referred to above. Sensor 126 cooperates with the power to motor 104 and command signals from the programming electronics to permit rotation of the motor shaft 106. For the embodiment described this would be a rotation of 180° each time. This allows incremental rotation of the Geneva wheel 102, one tooth, and the effective positioning of turntable 74 (and carousel) an increment equal to the distance needed to sample successive vials on alternate rows of circles.

The means which cooperate to effect this sampling between alternate rows by the probe, comprises cam 108, which as mentioned above, is secured to shaft 106. Arm 128 is pivotally mounted to block 130, which in turn, is secured to plate 100. Rotatably secured to the underside of arm 128 is cam follower 132, which follows the periphery of cam 108.

The free end of arm 128 is bent, in this embodiment, at right angles to the plane of the arm and includes a slotted portion 134. Arm 86 extending outward from the enclosure 82 protrudes through slot 134 and is biased against the inboard side of the slot by the action of spring 90. This results in arm 86 following the pivotal motion of arm 128.

To, perhaps, understand better the operation of the mechanism, a brief discussion of one cycle of operation is appropriate at this time. By way of illustration, assume the sample probe carrying means is in a down position such that the probe is in a vial in the outer circle. Having delayed in this position to allow an appropriate amount of sample to be read and analyzed by the system instrumentation, the programming electronics generate a signal which inhibits the operation of the appropriate one of the sensors, 72, so as to allow power to be supplied to motor 66. The latter rotates, and toothed belt 58 follows providing the necessary drive to the block assembly 48 and the probe carrying means thereby raising the latter.

Power is supplied to the motor 66 until the second one of the optical switch pair 72 senses the corresponding edge of the segment cutout 70, signalling full travel of the probe carrying means upward. The point on the periphery of the disc 68 where the cutout occurs in relationship to this latter switch (as well as the other member of the pair), of course, is a function of the distance to be travelled up or down by the probe carrying means. This design must insure that the end of the probe has cleared the top of the vial and the cover 38. The sensing switch of the pair 72 generates an appropriate electrical signal at this point which operates to inhibit sensor 126 (sensing notch 124, at this point), and thus enable motor 104 to drive shaft 106 and as a result, the Geneva rollers 118 and 120, 180°. The detent roller 120, if motion is presumed counterclockwise as viewed in FIG. 4, engages a corresponding notch in the detent wheel 102, causing it to incrementally rotate in response to the 180° movement of the roller 120.

Disc 110, secured to the axially mounted assembly, likewise rotates 180° and until notch 122 is positioned in the path of sensor 126. At this point, an electrical signal is generated which is transmitted to the programming electronics and operates to cut the power to motor 104 and the corresponding switch of the switch pair 72.

Simultaneous to the rotational movement just described, cam 108 which is part of the assembly axially mounted on shaft 106, likewise rotates the 180°. The high lobe contact with follower 132 which occurs in the initial position, reverts to contact with the low lobe of cam 108.

In the initial or high lobe contact position, arm 128 is pivoted outward from the internal mechanical assembly and through the cooperative action between itself and arm 86, positions the pivotally mounted square stock 56, and thus the probe carrying means, in a cooperating position with an opening in the outer circle. In responding to the low lobe position, the arm moves inward towards the internal mechanics under the return action of spring 90, causing the square stock to pivot inward so as to align the probe over a cooperating position in the next inner circle.

The optical sensor 126, having sensed completion of the 180° rotation by noting the "presence" of notch 122, as noted above, generates an appropriate electrical signal indicative of such. This signal inhibits the appropriate one of sensors 72 to allow motor 66 to be driven in a direction opposite to its most previous direction of rotation. This results in a lowering of the probe carrying means, and thus the sample probe, into the vial then positioned below it.

Again, sufficient delay is programmed into the electronics to allow sampling of this vial and, in time, an electrical signal is generated which keys the motor 66 to, again, reverse its direction of rotation so as to raise the probe. The sequence of events as outlined above continues. The assembly mounted on shaft 106 rotates (in the same direction at all times) so as to index the plate 102 and thus the carousel, one more position. The cam and cam follower cooperate to move arm 128 outward again, against the bias of spring 90, thus effecting a rotation of the probe carrying means to a cooperating position with the next vial in the outer row.

Alternate approaches to the simplified mechanics described above will be apparent to those of ordinary skill in the art in light thereof. One such approach involves the cam and cam follower action. It would include a fluted cam which would mount on the shaft 91 either above or below the Geneva wheel 102. The cam would be fluted so as to have a high and then a low lobe for successive teeth on the detent wheel. The cam follower 132 would cooperate with that cam so as to follow its action around the perimeter. The detent roller assembly, of course, would be positioned in a different location so that the cam follower could directly contact the fluted cam.

It should be apparent that additional concentric circles besides the two illustrated, can be added. Cam 108 can be modified to include more lobe positions thereon; the number of detent rollers, such as 118 and 120, increased; and other obvious changes so that the probe carrying means can trace an arc which takes it from one circle to the next, and to the next, etc. The position of the successive openings, in travelling from the outer to the inner row and then back out again would have to be located on the arc described by the hole (45) into which is positioned the probe, that hole having a radius equal to the length of the arm 18 as pivoted at the point of stock piece 56.

Additions to the above described assembly not particularly illustrated, would include means for sensing that the sample vials for a particular carousel has been completely analyzed. This could include an additional sensor such as those described earlier which would cooperate with an appropriate marking on the Geneva wheel 102 which would in turn give an appropriate signal or alarm signifying the end of the analysis for that particular carousel.

Other variations and modifications of the embodiment described should likewise be apparent to those of ordinary skill in the art.

The above is not to be considered a limitation on the breadth of the present invention which is to be found as set forth in the appended claims.

What is claimed is:

1. An automatic sampling transport system for sample vials comprising:
   (a) sample holding means including a plurality of openings disposed in at least two concentric circles of said openings, for depositing corresponding sample vials;
   (b) means for rotating the sample holding means;
   (c) sample probe carrying means;
   (d) means for raising and lowering said sample probe carrying means;
   (e) means for rotating said sample probe carrying means a predetermined arcuate length from a cooperating position with an opening in one of said concentric circles to a cooperating position with an opening in another of said concentric circles;
   (f) means for synchronously engaging said means for rotating said sample holding means and said means for rotating said sample probe carrying means, whereby the rotation of each of said means occurs simultaneously; and
   (g) means for synchronizing said rotation to the raising and lowering of said probe carrying means.

2. The system of claim 1 wherein said means for rotating said sample holding means comprises:
   (a) a geneva wheel assembly disposed about a first rotable shaft; and,
   (b) means for incrementally rotating said wheel assembly, including said first shaft, said sample holding means positioned on said first shaft; and wherein said means for synchronously engaging includes:
   (a) a motor, including a second shaft, said means for incrementally rotating said wheel assembly axially mounted to said second shaft;
   (b) an actuator cam axially connected to said second shaft;
   (c) a pivot arm connected to said means for rotating said sample probe carrying means; and
   (d) a cam follower positioned on said pivot arm, said follower contacting said activator cam and responsive to the rotational movement thereof about said second shaft, said pivot arm pivoting in response to the cooperative action between said cam and cam follower, such that said probe carrying means is rotating simultaneously with the pivoting of said arm.

3. An automatic fluid sampling transport system for sample vials used in sample analysis instruments comprising:
   (a) sample holding means including a plurality of openings disposed in at least two concentric circles of openings for depositing corresponding sample vials;
   (b) means for rotating said sample holding means;
   (c) sample probe carrying means;
   (d) means for raising and lowering said sample probe carrying means; and,
   (e) means for rotating said sample probe carrying means a predetermined arcuate length from a cooperating position with an opening in one of said concentric circles to a cooperating position with an opening in another of said concentric circles,
   (f) means for synchronizing the rotation of said sample holding means and said probe carrying means, to the raising and lowering of said probe carrying means including;
      (i) means for sensing when said probe carrying means is raised;
      (ii) means, responsive to said sensing means detecting when said probe carrying means is raised, for initiating said rotation;
      (iii) means for sensing when said rotation is complete:
      (iv) means responsive to said sensing means detecting when said rotation is complete, for initiating the lowering of said probe carrying means; and
      (v) means for sensing when the lowering of said probe carrying means is complete such that sample analysis can take place.

4. The system of claim 3 further comprising means for synchronously engaging said means for rotating said sample holding means and said means for rotating said sample probe carrying means, whereby the rotation of each of said means occurs simultaneously.

5. The systems of claim 4 wherein said means for rotating said sample holding means comprises:
   (a) a geneva wheel assembly disposed about a first rotatable shaft; and,
   (b) means or incrementally rotating said wheel assembly, including said shaft, said sample holding means positioned on said first shaft.

6. The system of claim 5 wherein said means for synchronously engaging includes:
   (a) a motor, including a second shaft, said means for incrementally rotating said wheel assembly axially mounted to said second shaft;
   (b) an actuator cam axially connected to said second shaft;
   (c) a pivot arm connected to said means for rotating said sample probe carrying means; and
   (d) a cam follower positioned on said pivot arm, said follower contacting said activator cam and responsive to the rotational movement thereof about said second shaft, said pivot arm pivoting in response to the cooperative action between said cam and cam follower, such that said probe carrying means is rotating simultaneously with the pivoting of said arm.

7. The sampling transport system of claim 6 comprising two said concentric circles of openings, the openings of the first such row disposed relative to the openings on the second of such rows such that they are substantially radially opposite the spacings between the openings on the second of such rows.

8. The sampling transport system of claim 7 wherein said sample holding means includes;
   (a) a circular tray having said openings disposed thereon; and,
   (b) a cover disposed over said openings, said cover having an opening through which the sample probe can pass to sample vials in any of the concentric circles.

9. An automatic fluid sampling transport system for sample vials used in sample analysis instruments comprising:
   (a) sample holding means including a plurality of openings disposed in at least two concentric circles of openings for depositing corresponding sample vials;
   (b) means for rotating said sample holding means comprising,
      (i) a geneva wheel assembly disposed about a first rotatable shaft; and
      (ii) means for incrementally rotating said wheel assembly, including said shaft, said sample holding means positioned on said first shaft;
   (c) sample probe carrying means:
   (d) means for raising and lowering said sample probe carrying means; and,
   (e) means for rotating said sample probe carrying means a predetermined arcuate length from a cooperating position with an opening in one of said concentric circles to a cooperative position with an opening in another of said concentric circles.

10. The system of claim 9 further comprising means for synchronously engaging said means for rotating said sample holding means and said means for rotating said sample probe carrying means, whereby the rotation of each said means occurs simultaneously, said means for synchronously engaging including:
   (a) a motor including a second shaft, said means for incrementally rotating said wheel assembly axially mounted to said second shaft;
   (b) an actuator cam axially connected to said second shaft;
   (c) a pivot arm connected to said means for roating said sample probe carrying means; and
   (d) a cam follower positioned on said pivot arm, said follower contracting said activator cam and responsive to the rotating movement thereof avout said second shaft,
   said pivot arm pivoting in response to the cooperative action between said cam and cam follower, such that said prove carrying means is rotating simultaneously with the pivoting of said arm.

* * * * *